United States Patent
Ugwu et al.

(10) Patent No.: US 11,260,028 B2
(45) Date of Patent: Mar. 1, 2022

(54) NANOSOME FORMULATIONS OF APREPITANT AND METHODS AND APPLICATIONS THEREOF

(71) Applicant: ForDoz Pharma Corp., East Windsor, NJ (US)

(72) Inventors: Sydney Ugwu, North Brunswick, NJ (US); Xin He, Green Brook, NJ (US); Zengli Fu, Kendall Park, NJ (US); Xin Teng, Cranbury, NJ (US); Ming Ji, Robbinsville, NJ (US)

(73) Assignee: ForDoz Pharma Corp., East Windsor, NJ (US)

( * ) Notice: Subject to any disclaimer, the term of this patent is extended or adjusted under 35 U.S.C. 154(b) by 0 days.

(21) Appl. No.: 16/626,408

(22) PCT Filed: Jun. 26, 2018

(86) PCT No.: PCT/US2018/039552
§ 371 (c)(1),
(2) Date: Dec. 24, 2019

(87) PCT Pub. No.: WO2019/005830
PCT Pub. Date: Jan. 3, 2019

(65) Prior Publication Data
US 2020/0138717 A1  May 7, 2020

Related U.S. Application Data

(60) Provisional application No. 62/524,662, filed on Jun. 26, 2017.

(51) Int. Cl.
| | | |
|---|---|---|
| *A61K 9/127* | (2006.01) |
| *A61K 9/00* | (2006.01) |
| *A61K 31/5377* | (2006.01) |
| *A61K 47/10* | (2017.01) |
| *A61K 47/14* | (2017.01) |
| *A61K 47/22* | (2006.01) |
| *A61K 47/24* | (2006.01) |
| *A61K 47/26* | (2006.01) |
| *A61K 47/28* | (2006.01) |
| *A61K 47/36* | (2006.01) |
| *A61K 45/06* | (2006.01) |

(52) U.S. Cl.
CPC .......... *A61K 9/1277* (2013.01); *A61K 9/0019* (2013.01); *A61K 31/5377* (2013.01); *A61K 47/10* (2013.01); *A61K 47/14* (2013.01); *A61K 47/22* (2013.01); *A61K 47/24* (2013.01); *A61K 47/26* (2013.01); *A61K 47/28* (2013.01); *A61K 47/36* (2013.01); *A61K 45/06* (2013.01)

(58) Field of Classification Search
CPC .... A61K 9/1277; A61K 9/0019; A61K 47/26; A61K 47/28; A61K 47/22; A61K 47/10; A61K 47/24; A61K 47/36; A61K 47/14; A61K 31/5377; A61K 45/06; A61K 9/127
See application file for complete search history.

(56) References Cited

U.S. PATENT DOCUMENTS

| | | | | |
|---|---|---|---|---|
| 5,154,930 | A * | 10/1992 | Popescu | A61K 9/0019 424/1.21 |
| 6,596,305 | B1 * | 7/2003 | Edgerly-Plug | A61K 9/1277 264/4.1 |
| 9,101,615 | B2 | 8/2015 | Wan et al. | |
| 2004/0247660 | A1 * | 12/2004 | Singh | A61P 25/18 424/450 |
| 2005/0175683 | A1 * | 8/2005 | Zhang | A61K 9/127 424/450 |
| 2011/0014270 | A1 * | 1/2011 | Holers | A61K 9/0019 424/450 |
| 2011/0038925 | A1 | 2/2011 | Wan et al. | |
| 2012/0164210 | A1 * | 6/2012 | Ueda | A61K 31/409 424/450 |
| 2013/0028959 | A1 * | 1/2013 | Malavia | A61K 31/683 424/450 |
| 2013/0129801 | A1 * | 5/2013 | Larsson | A23D 7/0053 424/401 |
| 2015/0202153 | A1 * | 7/2015 | Frank | A61K 31/357 424/450 |
| 2016/0082013 | A1 | 3/2016 | Ottoboni et al. | |
| 2016/0128964 | A1 * | 5/2016 | Arvidsson | A61K 9/0014 424/450 |

(Continued)

FOREIGN PATENT DOCUMENTS

| | | |
|---|---|---|
| CN | 105456228 | 4/2016 |
| CN | 105878250 | 8/2016 |

(Continued)

OTHER PUBLICATIONS

Hong, S et al in International Journal of Pharmaceutics, vol. 483, pp. 142-150, 2015.*
Aug. 31, 2021 Office Action from Chinese Patent Application No. 201880054132.9.
Aug. 31, 2021 Search Report from Chinese Patent Application No. 201880054132.9.

*Primary Examiner* — Gollamudi S Kishore
(74) *Attorney, Agent, or Firm* — Florek & Endres PLLC; Martin Endres

(57) ABSTRACT

Disclosed herein are pharmaceutical formulations of aprepitant suitable for parenteral administration including intravenous administration. The pharmaceutical formulations are stable and ready-to-use liposomes for the treatment of emesis and are particularly useful for treatment of chemotherapy or surgery-induced nausea and vomiting. Methods of preparation of the aprepitant formulations are also provided.

23 Claims, No Drawings

(56) References Cited

U.S. PATENT DOCUMENTS

2016/0193148 A1\* 7/2016 Giguere ................ A61K 9/127
424/450

FOREIGN PATENT DOCUMENTS

JP        2017 066059     \*   4/2017
WO     2012149376 A2    11/2012

\* cited by examiner

NANOSOME FORMULATIONS OF APREPITANT AND METHODS AND APPLICATIONS THEREOF

CROSS-REFERENCE TO RELATED APPLICATIONS

This application is the U.S. National Phase of International Patent Application No. PCT/US2018/039552, filed on Jun. 26, 2018, which claims priority under 35 U.S.C. § 119(e) to U.S. Provisional Application Ser. No. 62/524,662, filed on Jun. 26, 2017, the disclosures of which are incorporated herein by reference in their entirety

FIELD OF THE INVENTION

The disclosure relates generally to liposome formulations for the intravenous or parenteral administration of aprepitant for treatment of emesis. The liposome formulations are stable for prolonged periods of time. Also described are methods for preparing the stable aprepitant liposome pharmaceutical formulations.

BACKGROUND OF THE INVENTION

Aprepitant, with a chemical name 5-[[(2R,3S)-2-[(1R)-1-[3,5-bis(trifluoromethyl)phenyl] ethoxy]-3-(4-fluorophenyl)-4-morpholinyl]methyl]-1,2-dihydro-3H-1,2,4-triazol-3-one, has the structure:

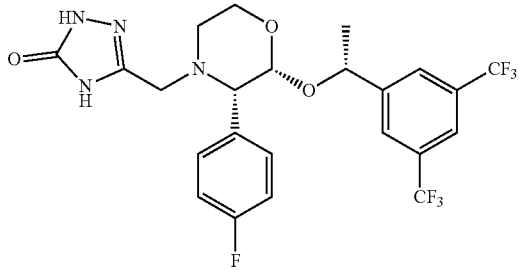 [SMILES: C[C@@H](O[C@H]1OCCN(Cc2n[nH]c(=O)[nH]2)[C@H]1c1ccc(F)cc1)c1cc(C(F)(F)F)cc(C(F)(F)F)c1]

or a triazinone tautomer.

This medication is also used to prevent nausea and vomiting after surgery. Aprepitant is currently available in the United States as an oral capsule; however, due to the nausea and vomiting experienced by patients, alternative formulations suitable for parenteral or intravenous administration would be desirable.

Liquid formulations containing aprepitant are very challenging to make due to the poor water solubility of aprepitant. Attempts have been made to overcome the poor aqueous solubility. For example, nanoparticulate formulations having a particle size of about 1000 nm were prepared and commercially marketed (EMEND®, Merck) for oral administration. Administration of this formulation yields a bioavailability of about 60-65%.

A lyophilized water-soluble prodrug salt form of aprepitant, foraprepitant (EMEND FOR INJECTION®, Merck), is commercially available for intravenous administration. Upon IV administration of a reconstituted formulation, foraprepitant is rapidly converted to aprepitant in vivo. However, the reconstituted material is only stable for 24 hours. Furthermore, this product contains polysorbate 80 surfactant. Polysorbate 80 is well known to cause allergic reactions, including the potential to cause anaphylaxis and infusion-site reactions which can lead to death. To minimize these reactions, foraprepitant is often administered with steroids; nevertheless, severe reactions are still frequently reported.

US 2013/0317016 A1 discloses aqueous formulations of aprepitant containing cosolvent and surfactant. Aprepitant was solubilized in cosolvent/surfactant systems and remained stable for 3 weeks. These formulations also contain surfactants (polysorbate 80, cremophor RH 40, poloxamer) that are well known to cause allergic reactions. Furthermore, the formulations contained co-solvents (dimethylacetamide, ethanol, PEG400) which are known to cause injection-related toxicities (e.g., phlebitis).

US 2016/0082013 A1 discloses emulsion formulations of aprepitant, which contain soybean oil, surfactant, co-surfactant, and ethanol for injectable administration. The formulation was reported to be stable for prolonged periods of time and is suitable for parenteral administration. Several disadvantages of this preparation include the presence of soybean oil which may lead to fat overload (high blood triglycerides), the presence of sodium oleate and ethanol which may cause injection-related reactions, high formulation pH which can cause pain during IV administration, and high concentration of egg lecithin which may also cause allergic reactions that can require premedication with steroids.

Therefore, new stable formulations are still needed, and in fact highly desirable, for administration of drugs like aprepitant.

SUMMARY OF THE INVENTION

The present invention was made to meet the foregoing need. It has now been discovered that a means of addressing the poor aqueous solubility, toxicity and stability issues of aprepitant is to prepare a nanoliposome formulation of aprepitant, which is suitable for IV administration. The nanoliposome formulation also further enhances the bioavailability of aprepitant.

One aspect of the disclosure is directed to an injectable liposome composition comprising: aprepitant; a phospholipid; a bilayer stabilizer; an antioxidant; an osmotic adjusting agent and/or a lyoprotectant; pH buffering agent; and water.

In some embodiments, the pH of the composition ranges from about 6.5 to about 7.5.

In some embodiments, the composition comprises about 1 wt % to about 12 wt % of the phospholipid.

In one embodiment of the liposome composition, the wt % ratio of the phospholipid to the aprepitant within the lipid bilayer phase of the liposome ranges from about 4:1 to about 12:1. Alternatively the wt % ratio of the phospholipid to the aprepitant within the bilayer phase of the liposome can range from about 12:1 to about 24:1.

In one embodiment of the liposome composition, the phospholipid has a melting temperature of about or less than 37° C. In some embodiments the phospholipid is selected from the group consisting of dioleoylphosphatidylcholine (DOPC), dimyristoylphosphatidylcholine (DMPC), dilauroylphosphatidylcholine (DLPC), soy phosphatidylcholine (SPC), and mixtures of two or more thereof. In some embodiments the bilayer stabilizer is cholesterol, or a derivative or analog thereof. In some embodiments, the antioxidant is selected from the group consisting of tocopherol, ascorbic acid, propyl gallate, butylated hydroxyanisole, butylated hydroxytoulene, and tiary butyl hydroquinone, or the like. In some preferred embodiments, the antioxidant is tocopherol. In some embodiments the osmotic adjusting agent is sucrose. In some embodiments the lyoprotectant is sucrose. In some embodiments the pH buffering agent is histidine.

Another aspect of the disclosure is directed to a method for preparing a pharmaceutical liposome composition comprising the steps of: dissolving aprepitant, phospholipid, cholesterol and tocopherol in an organic solvent to form a clear solution; evaporating the organic solvent from the clear solution to form a dried mixture; combining water, sucrose and histidine to form an aqueous solution; mixing the dried mixture with the aqueous solution to form a bulk liposome suspension; reducing the size of the liposomes in the bulk suspension; and sterilizing the liposome composition.

In one embodiment of the method, the size reduction of the liposomes is performed either by extruding the bulk liposome suspension through filters, or homogenizing the suspension. In one embodiment of the method, sterilizing the liposome composition is accomplished by filtering through a filter membrane having a pore size of about 0.2 µm or less. In one embodiment of the method, the organic solvent is ethanol or a mixture of ethanol and methylene chloride. In one embodiment of the method, evaporating the organic solvent is accomplished by rotary evaporation.

The liposome aprepitant formulation possesses advantages including good stability and prolonged circulation half-life, among others, which can be better appreciated in view of the following detailed description and claims.

DETAILED DESCRIPTION OF THE INVENTION

As disclosed herein, a number of ranges of values are provided. It is understood that each intervening value, to the tenth of the unit of the lower limit, unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither, or both limits are included in the smaller ranges is also encompassed within the invention, subject to any specifically excluded limit in the stated range. Where the stated range includes one or both of the limits, ranges excluding either or both of those included limits are also included in the invention.

The term "about" generally refers to plus or minus 10% of the indicated number. For example, "about 10%" may indicate a range of 9% to 11%, and "about 20" may mean from 18 to 22. Other meanings of "about" may be apparent from the context, such as rounding off, so, for example "about 1" may also mean from 0.5 to 1.4. Similarly, "about 0.2" may encompass the value 0.22.

As used herein, the singular forms "a", "an", and "the" include plural reference unless the context clearly dictates otherwise.

Any terms in the present application, unless specifically defined, will take the ordinary meanings as understood by a person of ordinary skill in the art.

In the present application, several nanoliposome formulations were prepared and characterized to identify a formulation and process that will allow aprepitant to be incorporated into the lipid bilayer to confer enhanced stability, enhanced solubility, and reduced toxicity. The disclosed formulation is polysorbate-free, oil-free, and solvent-free, has neutral pH, and contains a low concentration of phospholipids. These attributes render the formulation more stable and less toxic than previously disclosed formulations. A liquid or solid form of the formulation can be readily prepared according to the present invention. A solid form of the formulation is prepared by lyophilization of the liquid formulation, and possesses enhanced stability.

The inventive intravenous-injectable nanoliposomes are approximately 100 nm in size and can smoothly circulate in the bloodstream without causing capillary blockage and embolization. Furthermore, the nanoliposome formulations are physically and chemically stable for a prolonged period of time. The enhanced chemical stability is believed to be attributable to partitioning of aprepitant inside the lipid bilayer structure, thereby protecting the drug from precipitating or degrading in solution.

In one aspect, a pharmaceutical composition suitable for intravenous administration is provided, which comprises a stable liposome comprising a lipid bilayer phase, wherein the bilayer phase comprises aprepitant, a phospholipid, a bilayer stabilizing agent, an antioxidant, and an aqueous phase, where the aqueous phase comprises water, an osmotic adjusting agent and/or a lyoprotectant, a buffering agent, and a pH-adjusting agent.

Lyoprotectants are molecules which protect freeze-dried material. These molecules are typically polyhydroxy compounds such as sugars (monosaccharides, disaccharides, or polysaccharides), polyalcohols, and their derivatives. Sucrose and trehalose are naturally occurring lyoprotectants. Sucrose is an example of preferred lyoprotectants for the inventive compositions.

In one embodiment, the composition is a liposome comprising a phospholipid, including but not limited to dioleoylphosphatidylcholine (DOPC), soy phosphatidylcholine (SPC), dimyristoylphosphatidylcholine (DMPC), or dilauroylphosphatidylcholine (DLPC), or a mixture of two or more thereof.

While not intended to be limiting, the composition typically contains about 1 wt % to about 12 wt % of phospholipid(s).

In one embodiment, the composition comprises about 4 wt % to about 10 wt % of phospholipid(s).

In one embodiment, the composition comprises about 5 wt % to about 9 wt % of phospholipid(s).

In one embodiment, the composition comprises about 6 wt % to about 8 wt % of phospholipid(s).

In one embodiment, the composition comprises about 7 wt % to about 8 wt % of phospholipid(s).

In one embodiment, the composition comprises about 1 wt % to about 6 wt % of phospholipid(s).

While not intended to be limiting, the ratio of phospholipid to aprepitant (wt %:wt %) in the composition typically ranges from about 4:1 to about 24:1.

In one embodiment, the ratio of phospholipid to aprepitant (wt %:wt %) in the composition ranges from about 4:1 to about 12:1, or about 6:1 to about 10:1, or about 7:1 to about 9:1, or about 8:1 to about 9:1.

In one embodiment, the ratio of phospholipid to aprepitant (wt %:wt %) in the composition ranges from about 4:1 to about 12:1.

In one embodiment, the ratio of phospholipid to aprepitant (wt %:wt %) in the composition ranges from about 6:1 to about 10:1.

In one embodiment, the ratio of phospholipid to aprepitant (wt %:wt %) in the composition ranges from about 7:1 to about 9:1.

In one embodiment, the ratio of phospholipid to aprepitant (wt %:wt %) in the composition ranges from about 8:1 to about 9:1.

In one embodiment, the ratio of phospholipid to aprepitant (wt %:wt %) in the composition ranges from about 12:1 to about 24:1.

In another embodiment, the bilayer stabilizer is cholesterol, or cholesteryl sulfate, or a derivative or analog thereof.

In one embodiment, the composition comprises an antioxidant. In some embodiments, the antioxidants include, but are not limited to, tocopherol, ascorbic acid, propyl gallate, butylated hydroxyanisole, butylated hydroxytoulene, and tiary butyl hydroquinone. In a further embodiment, the antioxidant is alpha-tocopherol.

In another embodiment the composition comprises an aqueous phase which comprises an osmotic adjusting agent. In some preferred embodiments, the osmotic adjusting agent is sucrose.

In one embodiment, the composition comprises a buffer or buffering agent. In some preferred embodiments, the buffering agent is histidine.

In another embodiment, the buffer is selected from the group consisting of phosphate buffer, citrate buffer, Tris buffer, carbonate buffer, succinate buffer, maleate buffer, and borate buffer.

In another embodiment, the buffer is selected from the group consisting of phosphate buffered saline (PBS) and citrate buffer.

In one embodiment, the osmotic agent is a pharmaceutically acceptable organic compound selected from the group consisting of glycerol, sorbitol, xylitol, mannitol, glucose, trehalose, maltose, sucrose, raffinose, lactose, dextran, polyethylene glycol, and propylene glycol.

In another embodiment, the osmotic agent is a pharmaceutically acceptable inorganic salt such as sodium chloride, mixtures of sodium chloride and one or more other pharmaceutically acceptable inorganic salts, or the like.

In one embodiment, the pH adjusting agent is selected from the group consisting of sodium hydroxide, potassium hydroxide, magnesium hydroxide, sodium carbonate, Tris, sodium linoleate, sodium oleate, potassium carbonate, potassium linoleate, potassium oleate, and mixtures of two or more thereof.

In one embodiment, the composition has a pH of about 8 to about 9, about 7 to about 8, or about 6 to about 7. In some preferred embodiments, the pH is in the range 6 to 7.

In one embodiment, the composition is a stable system maintaining an intensity—weighted mean particle size in the range of about 50 nm to about 200 nm, or about 50 to about 250 nm, or about 50 nm to about 300 nm, as determined by dynamic light scattering (DLS).

In another embodiment, the mean particle size is maintained between or above 100 nm to 120 nm for a period of at least 1 month at both refrigerator temperature (3 to 5° C.) and room temperature.

In another aspect, a method for preparing a liposome comprising aprepitant, which is suitable for parenteral or intravenous administration, is provided.

In one embodiment, the method comprises: a) preparing a lipid phase by dissolving aprepitant, phospholipid, and tocopherol in ethanol or a mixture of ethanol-methylene chloride, then evaporating the ethanol or ethanol-methylene chloride to generate a dried aprepitant-lipid mixture; b) preparing an aqueous phase by mixing water, optionally with an osmotic agent and optionally with a buffer, to generate an aqueous mixture; c) combining the dried aprepitant-lipid mixture and the aqueous mixture and mixing them together to generate a bulk liposome; and d) subjecting the bulk liposome to filter extrusion or high pressure homogenization to generate a nanoliposome.

In another embodiment, the method comprises: a) preparing a lipid phase by dissolving aprepitant, phospholipid, and tocopherol in ethanol or a mixture of ethanol-methylene chloride; b) preparing an aqueous phase by mixing water, optionally with an osmotic agent and optionally with a buffer, to generate an aqueous mixture; c) adding aqueous phase to the aprepitant-phospholipid-tocopherol mixture and mixing to generate bulk liposome suspension; d) subjecting the bulk liposome to filter extrusion or high pressure homogenization; and e) removing the ethanol or ethanol-methylene chloride from the liposome suspension.

Any components disclosed for the liposome formulations according to any embodiments are applicable to the methods and processes of preparation disclosed herein, as a person of ordinary skill in the art would readily understand.

In one embodiment the organic solvent or solvents are removed by rotary evaporation.

In one embodiment, the method further comprises sterilizing the nanoliposomes to generate the final sterile liposomes, wherein the final liposomes are suitable for injection into a subject. In some preferred embodiments, sterilization is accomplished by filtering a liquid nanoliposome preparation through a sterilizing filter. In some preferred embodiments, the filter is a membrane filter having a pore size of about 0.2 μm or less.

As noted above, aprepitant can exist in a chemical structure of formula:

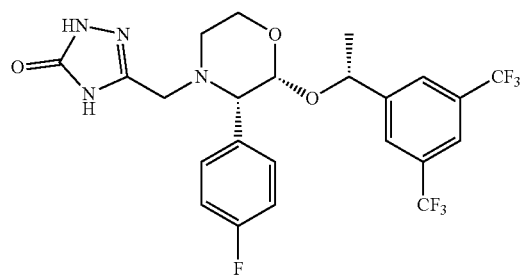 [SMILES: C[C@@H](O[C@H]1OCCN(Cc2n[nH]c(=O)[nH]2)[C@H]1c1ccc(F)cc1)c1cc(C(F)(F)F)cc(C(F)(F)F)c1]

which may also exist in the form of a triazolinone tautomeric structure:

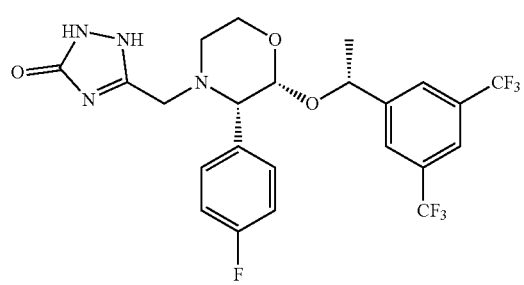 [SMILES: C[C@@H](O[C@H]1OCCN(Cc2nc(=O)[nH][nH]2)[C@H]1c1ccc(F)cc1)c1cc(C(F)(F)F)cc(C(F)(F)F)c1]

Alternatively the triazolinone moiety may exist in the form of following hydroxy tautomers or the like:

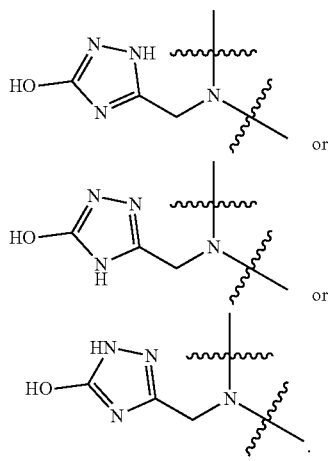

All of these forms of aprepitant in any formulations disclosed herein are encompassed by the present invention.

In another aspect, the present invention provides a method of preventing or treating nausea and/or vomiting in a subject associated with chemotherapy and/or after surgery, the method comprising administration of a therapeutically effective amount of a liposome composition comprising aprepitant according to any embodiment disclosed herein to the subject.

Regimens that are linked to a high incidence (90% or higher) of nausea and vomiting are referred to as "highly emetogenic chemotherapy", and those causing a moderate incidence (30-90%) of nausea and vomiting are referred to as "moderately emetogenic chemotherapy". The inventive formulations are useful for the prevention of acute and delayed nausea and vomiting associated with initial and repeated courses of both highly emetogenic cancer chemotherapy and moderately emetogenic cancer chemotherapy, in particular the former.

Aprepitant helps prevent nausea/vomiting through blocking one of the body's natural substances (substance P/neurokinin 1, or NK1). The liposome formulations of aprepitant disclosed herein may be used alone or in combination with other antiemetic agents, including other NK1 receptor antagonists, for example, casopitant and rolapitant. In addition, the inventive liposome formulation of aprepitant may be used in conjunction with other types of antiemetic agents, including but not limited to 5-$HT_3$ receptor antagonists, dopamine antagonists, antihistamines (Hi histamine receptor antagonists), cannabinoids (e.g., *cannabis* or extracts, dronabinol, or synthetic cannabinoids, such as nabilone), benzodiazepines (e.g., midazolam and lorazepam), anticholinergics (e.g., hyoscine), steroids (e.g., dexamethasone), or the like.

Examples of 5-$HT_3$ receptor antagonists include, but are not limited to, dolasetron, granisetron, mirtazapine, ondansetron, palonosetron, and tropisetron; examples of dopamine antagonists include, but are not limited to, domperidone, olanzapine, droperidol, haloperidol, chlorpromazine, prochlorperazine, alizapride, prochlorperazine, and metoclopramide; and examples of antihistamines include, but are not limited to, cinnarizine, cyclizine, diphenhydramine, dimenhydrinate, doxylamine, meclizine, promethazine, and hydroxyzine. Other antiemetic agents include, but are not limited to, trimethobenzamide, emetrol, propofol, and muscimol.

In another aspect, the present invention provides use of a liposome aprepitant composition according to any embodiments disclosed herein in the manufacture of medicament for the prevention or treatment of nausea and/or vomiting associated with chemotherapy and/or after surgery of a patient.

The formulations may be presented in unit-dose or multi-dose sealed containers, for example, ampoules and vials, and may be ready for injection or be stored in a lyophilized condition requiring only the addition of the sterile liquid carrier, for example water, for injection immediately prior to use.

As noted above, parenteral or intravenous administration is preferable to oral administration for this utility due to the nausea and vomiting experienced by patients undergoing such treatment. The liposome aprepitant formulation of the present invention is suitable for parenteral or intravenous administration, providing numerous benefits than the existing tablet or capsule forms as generally known to those skilled in the art for other liposome formulations, among which it provides high stability and prolonged circulation half-life in the body.

EXAMPLES

The following examples are illustrative in nature and are not intended to be limiting. Preparation of Aprepitant Nanoliposomes for Intravenous Injection Example 1. Aprepitant DOPC Nanoliposome Preparation, 3 mg/mL To prepare the aprepitant nanoliposomes, 30 mg Aprepitant, 226 mg DOPC and 0.64 mg Tocopherol was dissolved in 99% Ethanol. This resulting mixture was evaporated at 40° C. in a Rotary Evaporator for 10 minutes. Next, 8.4 grams sucrose and 155 mg Histidine were dissolved in 100 mL of purified water. The pH of the sucrose/histidine buffer was adjusted with 1.0 M HCl or 1.0 M NaOH to 7.06. The Sucrose/Histidine buffer was filtered through a 0.22 µm PES membrane filter. Ten mL of Sucrose/Histidine buffer was added to the dried Aprepitant/DOPC mixture and mixed at 200 rpm at 40° C. for 5 minutes to form a homogenous bulk liposome suspension. The bulk liposome suspension was extruded through double-stacked polycarbonate filters at room temperature using an Avestin™ Homogenizer/Extruder. The following filters were used:
  i) 200 nm sized filter
  ii) 100 nm sized filter
  iii) 80 nm sized filter The pH of the final sized nanoliposome suspension was measured. Then, the final sized nanoliposome mixture was sterile filtered through a 0.22 µm PES membrane filter. The filtered nanoliposome suspension was filled into Schott Type Glass vials and stoppered with West Grey Stoppers. The details of the nanoliposome suspension composition are shown in Table 1, and the in-process data is summarized in Tables 2 and 3. The final nanoliposome suspension was a translucent white suspension. The intensity-weighted mean particle size diameter measured by dynamic light scattering (DLS) (Nicomp™ Particle Sizer) was 102 nm. The zeta potential measured by laser Doppler micro-electrophoresis (Malvern™ Zetasizer Nano ZS®) was found to be −25.4 mV. The pH of the nanoliposome was 7.01. Greater than ninety-nine percent (99%) of aprepitant was entrapped inside the phospholipid bilayers as determined by gel filtration (G-25) and HPLC methods. This aprepitant-containing liposome preparation can be injected as is, or diluted with 5% dextrose or 0.9% saline for infusion.

TABLE 1

| Composition | |
|---|---|
| Ingredients | Concentration (mg/mL) |
| Aprepitant | 3 mg/mL |
| DOPC | 22 mg/mL |
| Tocopherol | 0.064 mg/mL |
| Sucrose | 84 mg/mL |
| Histidine | 1.55 mg/mL |
| Sodium Hydroxide qs | To adjust pH to ~7.0 |
| Hydrochloric Acid qs | To adjust pH to ~7.0 |

TABLE 2

In-Process Particle Size Data Summary

| Filter size (nm) | Mean Diameter (nm) | 99 Percentile size < (nm) |
|---|---|---|
| 200 | 182.8 | 465.9 |
| 100 | 135.7 | 252.6 |
| 80 | 103.6 | 238.6 |
| 200 nm Sterile Filtered | 102.4 | 229.2 |

TABLE 3

In-process Analytical Data Summary

| Parameter | Results |
|---|---|
| Appearance | White translucent suspension, with no visible precipitates |
| pH | 7.01 |
| Zeta Potential (mV) | −25.4 |
| Osmolality (mOsm/Kg) | 358 |
| Aprepitant assay (mg/mL) | 2.93 |
| Entrapment Efficiency (%) | 99.8 |

Example 2. Aprepitant DMPC Nanoliposome Preparation, 4 mg/mL

To prepare aprepitant nanoliposomes, 80 mg Aprepitant, 710 mg DMPC, and 1.28 mg Tocopherol was dissolved in 99% Ethanol:Methylene Chloride (1:1) mixture. This resulting mixture was evaporated to dryness at 40° C. in a Rotary Evaporator for 10 minutes. Next, 8.4 grams sucrose and 155 mg Histidine was dissolved in 100 mL purified water. The pH of the sucrose/histidine buffer was adjusted with 1.0 M HCl or 1.0 M NaOH to 7.08. The Sucrose/Histidine buffer was filtered through a 0.22 μm PES membrane filter. Twenty mL of Sucrose/Histidine Buffer was added to the dried Aprepitant/DMPC mixture and mixed at 200 rpm at 40° C. for 5 minutes to form a homogenous bulk liposome suspension. The bulk liposome suspension was then extruded through double-stacked polycarbonate filters at room temperature using an Avestin™ Homogenizer/Extruder. The following filters were used:
  i) 200 nm sized filter
  ii) 100 nm sized filter
  iii) 80 nm sized filter The pH of the final sized nanoliposome suspension was measured. Then, the final sized nanoliposome suspension was sterile filtered through a 0.22 μm PES membrane filter. The filtered nanoliposomes was filled into Schott Type Glass vials and stoppered with West Grey Stoppers. The details of the nanoliposome composition are summarized in Table 4 and the in-process data is summarized in Tables 5 and 6. The final nanoliposome suspension was a translucent white suspension with no visible particulates. The intensity-weighted mean particle size diameter measured by dynamic light scattering (Nicomp™ Particle Sizer) was 110 nm. The zeta potential measure by Laser Doppler micro-electrophoresis (Malvern™ Zetasizer ZS®) was found to be 26.1 mV. The pH of the nanoliposomes was 6.92. Greater than 99 percent of aprepitant was entrapped inside the phospholipid bilayers as determined by gel filtration (G-25) and HPLC methods. This aprepitant-containing liposome preparation can be injected as is, or diluted with 5% dextrose or 0.9% saline for infusion.

TABLE 4

| Composition | |
|---|---|
| Ingredients | Concentration (mg/mL) |
| Aprepitant | 4 mg/mL |
| DMPC | 36 mg/mL |
| Tocopherol | 0.064 mg/mL |
| Sucrose | 84 mg/mL |
| Histidine | 1.55 mg/mL |
| Sodium Hydroxide qs | To adjust pH to ~7.0 |
| Hydrochloric Acid qs | To adjust pH to ~7.0 |

TABLE 5

In-Process Particle Size Data Summary

| Filter size (nm) | Mean Diameter (nm) | 99 Percentile size < (nm) |
|---|---|---|
| 200 | 207.4 | 472.4 |
| 100 | 145.3 | 304.2 |
| 80 | 115.6 | 237.2 |
| 200 nm Sterile Filtered | 111.2 | 176.1 |

TABLE 6

In-process Analytical Data Summary

| Parameter | Results |
|---|---|
| Appearance | White translucent suspension, with no visible precipitates |
| pH | 6.85 |
| Zeta Potential (mV) | −26.1 |
| Osmolality (mOsm/Kg) | 343 |
| Aprepitant assay (mg/mL) | 3.96 |
| Entrapment Efficiency (%) | 99.5 |

Example 3. Aprepitant SPC Nanoliposome Preparation, 4 mg/mL

To prepare aprepitant liposomes, 80 mg Aprepitant, 807 mg SPC and 1.28 mg Tocopherol was dissolved in 99% Ethanol:Methylene Chloride (1:1) mixture. This resulting mixture was evaporated to dryness at 40° C. in a Rotary Evaporator for 10 minutes. Next, 8.4 grams sucrose and 155 mg Histidine was dissolved in 100 mL purified water. The pH of the sucrose/histidine buffer was adjusted with 1.0 M HCl or 1.0 M NaOH to 7.00. The Sucrose/Histidine buffer was filtered through a 0.22 μm PES membrane filter. Twenty mL of Sucrose/Histidine Buffer was added to the dried Aprepitant/SPC mixture and mixed at 200 rpm at 40° C. for 5 minutes to form a homogenous bulk liposome suspension. The bulk liposome suspension was then extruded through double-stacked polycarbonate filters at room temperature using an Avestin™ Homogenizer/Extruder. The following filters were used:

i) 200 nm sized filter
ii) 100 nm sized filter
iii) 80 nm sized filter

The pH of the final sized nanoliposome suspension was measured. Then the final sized nanoliposome suspension was sterile filtered through a 0.22 μm PES membrane filter. The filtered nanoliposomes was filled into Schott Type Glass vials and stoppered with West Grey Stoppers. The details of the nanoliposome composition are summarized in Table 7 and the in-process data is summarized in Tables 8 and 9. The final nanoliposome suspension was a translucent white suspension with no visible particulates. The intensity-weighted mean particle size diameter measured by dynamic light scattering (Nicomp™ Particle Sizer) was 110 nm. The zeta potential measure by Laser Doppler micro-electrophoresis (Malvern™ Zetasizer ZS®) was found to be 26.1 mV. The pH of the nanoliposomes was 6.92. Greater than 99% of aprepitant was entrapped inside the phospholipid bilayers as determined by gel filtration (G-25) and HPLC methods. This aprepitant-containing liposomes can be injected as is, or diluted with 5% dextrose or 0.9% saline for infusion.

TABLE 7

| Composition | |
| --- | --- |
| Ingredients | Concentration (mg/mL) |
| Aprepitant | 4 mg/mL |
| SPC | 36 mg/mL |
| Tocopherol | 0.064 mg/mL |
| Sucrose | 84 mg/mL |
| Histidine | 1.55 mg/mL |
| Sodium Hydroxide qs | To adjust pH to ~7.0 |
| Hydrochloric Acid qs | To adjust pH to ~7.0 |

TABLE 8

| In-Process Particle Size Data Summary | | |
| --- | --- | --- |
| Filter size (nm) | Mean Diameter (nm) | 99 Percentile size < (nm) |
| 200 | 225.4 | 449.6 |
| 100 | 136.2 | 243.4 |
| 80 | 117.9 | 266.9 |
| 200 nm Sterile Filtered | 115.2 | 175.7 |

TABLE 9

| In-process Analytical Data Summary | |
| --- | --- |
| Parameter | Results |
| Appearance | White translucent suspension, with no visible precipitates |
| pH | 7.01 |
| Zeta Potential (mV) | −25.8 |
| Osmolality (mOsm/Kg) | 406 |
| Aprepitant assay (mg/mL) | 3.91 |
| Entrapment Efficiency (%) | 99.2 |

Example 4. Stability of the Aprepitant Nanoliposome Suspension at Refrigerator (2-8° C.) and 25° C./60% Relative Humidity (RH)

Stability of the aprepitant nanoliposomes prepared as described in Example 1 was measured by storing the nanoliposome preparation at 25° C./60% RH or at 2-8° C. (refrigerator temperature). The summary stability data is shown in Table 10. Mean particle size measured using DLS remained essentially unchanged for 4 weeks at both storage temperatures. The nanoliposomes were also inspected by microscopy for aprepitant crystals but no visible particulates were observed. Aprepitant assay as determined by HPLC method remained unchanged for 4 weeks at both storage temperatures. However, nanoliposomes stored at 2-8° C. appear to be slightly more stable.

TABLE 10

Stability of Aprepitant Nanoliposomes prepared according to methods in Example 1

| Formulation | Temperature | Time | Mean Diameter (nm) | HPLC Assay (% of initial) |
| --- | --- | --- | --- | --- |
| Example 1 | 25° C./60% RH | Initial | 103.6 | 100 |
| | | 1 week | 104.1 | 99.2 |
| | | 2 week | 102.6 | 99.6 |
| | | 4 week | 104.1 | 99.1 |
| | 2-8° C. | Initial | 103.6 | 100 |
| | | 1 week | 103.8 | 99.7 |
| | | 2 week | 102.9 | 99.0 |
| | | 4 week | 101.9 | 99.5 |

Stability of the aprepitant nanoliposomes prepared as described in Examples 2 was measured by storing the nanoliposome preparation at 25° C./60% RH or at 2-8° C. The summary stability data is shown in Table 11. The mean particle size measured using DLS remained essentially unchanged for 6 months at both storage temperatures. The nanoliposomes were also inspected by microscopy for aprepitant crystals, but no visible particulates were observed. Aprepitant assay as determined by HPLC method remained essentially unchanged for 6 months at both storage temperatures.

TABLE 11

Stability of Aprepitant Nanoliposome prepared according to methods in Example 2

| Formulation | Temperature | Time | Mean Diameter (nm) | HPLC Assay (% of initial) |
| --- | --- | --- | --- | --- |
| Example 2 | 25° C./60% RH | Initial | 114.0 | 100 |
| | | 1 month | 117.7 | 97.1 |
| | | 3 month | 117.8 | 98.5 |
| | | 6 month | 117.2 | 98.2 |
| | 2-8° C. | Initial | 114.0 | 100 |
| | | 3 month | 115.6 | 99.7 |
| | | 6 month | 116.2 | 99.0 |

Example 5. Freeze-Drying of Aprepitant Nanoliposomes

Aprepitant nanoliposomes prepared as described in Example 2 were subjected to lyophilization. Vials containing 1 mL of aprepitant nanoliposomes were frozen at −47° C. for 4 hours and then freeze dried at −20° C. and 100 mTorr pressure for 48 hours followed by secondary drying at 25° C. and 100 mT pressure for 6 hours. After lyophilization, 0.9 mL purified water was added to the dried cake and gently shaken for 1 min to redisperse the liposomes. Prior to lyophilization, the mean particle diameter of the liposomes was 111.2 nm and after lyophilization, the mean particle diameter was 114.8 nm. There was no significant change in particle size after lyophilization.

Example 6. Stability of the Aprepitant Nanoliposomes to Freeze-Thaw Cycle

The aprepitant nanosuspension prepared according to Examples 1, 2, and 3 were tested for stability upon exposure to a freeze-thaw cycle. Samples from the Examples 1, 2, and 3 were stored at −20° C. for 4 hours. Then they were thawed at room temperature for 1 hour. The freeze-thaw cycle was repeated once. Prior to freezing, all samples did not present any visible particles under the microscope. After freeze and thaw, no visible particulates were observed under the microscope. The mean particle size prior to freezing was 114.1 nm and after thawing was 110.8 nm. This experiment concluded that aprepitant nanoliposomes are stable to freeze-thaw cycle. This may be attributed to the presence of sucrose in the formulation which acts as a cryoprotectant as well as a lyoprotectant.

Drug loading and drug retention inside liposome bilayer are two of the most challenging tasks of incorporating hydrophobic drugs such as Aprepitant inside liposome bilayers. This applied to early trials of Aprepitant liposomal formulations disclosed herein. The present inventors successfully achieved high loading of aprepitant inside the bilayers; however, upon storage at room temperature, aprepitant migrated out of the bilayer and precipitated in solution. The present inventors discovered with surprise that in the presence of tocopherol, aprepitant was retained in the bilayer for extended period of time, which allowed preparation of stable formulations. This result was surprising since tocopherol is also a hydrophobic molecule.

The above-described aspects of the invention as well as the disclosed embodiments thereof are meant to be exemplary and illustrative, not limiting in scope. Various changes and modifications to the disclosed examples or embodiments will be apparent to those skilled in the art based on the present disclosure, and such changes and modifications, including but not limited to those relating to the formulations and/or methods of preparation, may be made without departure from the spirit and scope of the present invention.

What is claimed is:

1. An injectable aprepitant pharmaceutical composition comprising: (a) water; and (b) aprepitant liposomes wherein the aprepitant liposomes comprise:
   (i) aprepitant;
   (ii) a phospholipid selected from the group consisting of dioleoylphosphatidylcholine (DOPC), dimyristoylphosphatidylcholine (DMPC), dilauroylphosphatidylcholine (DLPC), soy phosphatidylcholine (SPC), and mixtures of two or more thereof; and
   (iii) tocopherol
   wherein the wt %:wt % ratio of phospholipid to aprepitant is about 4:1 to about 12:1; the wt:wt ratio of tocopherol to phospholipid is about 1:343.75 to about 1:562.5; and the liposomes have an intensity weighted mean particle size of about 50 nm to about 300 nm as determined by dynamic light scattering and the composition is polysorbate free, oil free and solvent free and after storage of the composition in a glass vial with a stopper at 25° C. or 2-8° C. for four weeks the composition shows no visible signs of aprepitant crystals when inspected by microscopy.

2. The injectable aprepitant pharmaceutical composition of claim 1 further comprising an osmotic adjusting agent, a lyoprotectant, a buffering agent, a pH adjusting agent or a combination of the foregoing.

3. The injectable aprepitant pharmaceutical composition of claim 1, wherein the aprepitant liposomes further comprise cholesterol or cholesteryl sulfate.

4. The injectable aprepitant pharmaceutical composition of claim 2 wherein the osmotic adjusting agent is selected from the group consisting of glycerol, sorbitol, xylitol, mannitol, glucose, trehalose, maltose, sucrose, raffinose, lactose, dextran, polyethylene glycol, and propylene glycol; a pharmaceutcially acceptable inorganic salt or any combination thereof.

5. The injectable aprepitant pharmaceutical composition of claim 2 wherein the lyoprotectant is selected from the group consisting of monosaccharides, disaccharides, polysaccharides, polyalcohols, and combinations thereof.

6. The injectable aprepitant pharmaceutical composition of claim 2 wherein the pH buffering agent is selected from the group consisting of histidine, phosphate buffer, citrate buffer, Tris buffer, carbonate buffer, succinate buffer, maleate buffer, borate, and combinations thereof.

7. The injectable aprepitant pharmaceutical composition of claim 1 wherein the wt %:wt % ratio of phospholipid to aprepitant is about 6:1 to about 10:1.

8. The injectable aprepitant pharmaceutical composition of claim 1 wherein the wt %:wt % ratio of phospholipid to aprepitant is about 7:1 to about 9:1.

9. An injectable aprepitant pharmaceutical composition consisting of:
   (a) water;
   (b) an osmotic agent and/or a lyoprotectant;
   (c) a pH buffering agent; and
   (d) aprepitant liposomes wherein the aprepitant liposomes consist of:
   (i) aprepitant;
   (ii) a phospholipid selected from the group consisting of dioleoylphosphatidylcholine (DOPC), dimyristoylphosphatidylcholine (DMPC), dilauroylphosphatidylcholine (DLPC), soy phosphatidylcholine (SPC), and mixtures of two or more thereof;
   (iii) tocopherol; and
   (iv) optionally a bilayer stabilizer selected from the group consisting of cholesterol and cholesteryl sulfate
   wherein the wt %:wt % ratio of phospholipid to aprepitant is about 4:1 to about 12:1; the wt:wt ratio of tocopherol to phospholipid is about 1:343.75 to about 1:562.5; the liposomes have an intensity weighted mean particle size of about 50 nm to about 300 nm as determined by dynamic light scattering and the pharmaceutical composition has a pH of about 6 to about 8 and after storage of the composition in a glass vial with a stopper at 25° C. or 2-8° C. for four weeks the composition shows no visible signs of aprepitant crystals when inspected by microscopy.

10. The injectable aprepitant pharmaceutical composition of claim 9 wherein the osmotic agent and/or lyoprotectant is sucrose.

11. The injectable aprepitant pharmaceutical composition of claim 9 wherein the pH buffering agent is histidine.

12. The injectable aprepitant pharmaceutical composition of claim 9 wherein the wt %:wt % ratio of phospholipid to aprepitant is about 6:1 to about 10:1.

13. The injectable aprepitant pharmaceutical composition of claim 9 wherein the wt %:wt % ratio of phospholipid to aprepitant is about 7:1 to about 9:1.

14. The injectable aprepitant pharmaceutical composition of claim 9 wherein the osmotic agent and/or lyoprotectant comprises sucrose and the pH buffering agent comprises histidine
wherein the wt %:wt % ratio of phospholipid to aprepitant is about 6:1 to about 10:1; the liposomes have an intensity weighted mean particle size of about 50 nm to about 250 nm as determined by dynamic light scattering and the pharmaceutical composition has a pH of about 6 to about 8.

15. The injectable aprepitant pharmaceutical composition of claim 9 wherein the bilayer stabilizer is not present.

16. The injectable aprepitant pharmaceutical composition of claim 1 wherein the wt:wt ratio of tocopherol to phospholipid is about 1:343.75 to about 1:562.5 and the wt:wt ratio of tocopherol to aprepitant is about 1:46.875 to about 1:62.5.

17. The injectable aprepitant pharmaceutical composition of claim 9 wherein the wt:wt ratio of tocopherol to phospholipid is about 1:343.75 to about 1:562.5 and the wt:wt ratio of tocopherol to aprepitant is about 1:46.875 to about 1:62.5.

18. The injectable aprepitant pharmaceutical composition of claim 1 wherein the liposomes comprise tocopherol, DOPC and aprepitant and the wt:wt ratio of tocopherol to DOPC is about 1:343.75 and the wt:wt ratio of tocopherol to aprepitant is about 1:46.875.

19. The injectable aprepitant pharmaceutical composition of claim 1 wherein the liposomes comprise tocopherol, DMPC and aprepitant and the wt:wt ratio of tocopherol to DMPC is about 1:562.5 and the wt:wt ratio of tocopherol to aprepitant is about 1:62.5.

20. The injectable aprepitant pharmaceutical composition of claim 1 wherein the liposomes comprise tocopherol, SPC and aprepitant and the wt:wt ratio of tocopherol to DMPC is about 1:562.5 and the wt:wt ratio of tocopherol to aprepitant is about 1:62.5.

21. The injectable aprepitant pharmaceutical composition of claim 9 wherein the liposomes comprise tocopherol, DOPC and aprepitant and the wt:wt ratio of tocopherol to DOPC is about 1:343.75 and the wt:wt ratio of tocopherol to aprepitant is about 1:46.875.

22. The injectable aprepitant pharmaceutical composition of claim 9 wherein the liposomes comprise tocopherol, DMPC and aprepitant and the wt:wt ratio of tocopherol to DMPC is about 1:562.5 and the wt:wt ratio of tocopherol to aprepitant is about 1:62.5.

23. The injectable aprepitant pharmaceutical composition of claim 9 wherein the liposomes comprise tocopherol, SPC and aprepitant and the wt:wt ratio of tocopherol to DMPC is about 1:562.5 and the wt:wt ratio of tocopherol to aprepitant is about 1:62.5.

* * * * *